(12) United States Patent
Neumann

(10) Patent No.: US 11,393,572 B2
(45) Date of Patent: Jul. 19, 2022

(54) SYSTEM AND METHOD FOR MODIFYING A NUTRITION REQUIREMENT

(71) Applicant: KPN INNOVATIONS, LLC., Lakewood, CO (US)

(72) Inventor: Kenneth Neumann, Lakewood, CO (US)

(73) Assignee: KPN INNOVATIONS, LLC., Lakewood, CO (US)

( * ) Notice: Subject to any disclaimer, the term of this patent is extended or adjusted under 35 U.S.C. 154(b) by 9 days.

(21) Appl. No.: 17/087,700

(22) Filed: Nov. 3, 2020

(65) Prior Publication Data

US 2022/0139523 A1   May 5, 2022

(51) Int. Cl.
| | |
|---|---|
| *G16H 20/60* | (2018.01) |
| *G16H 50/70* | (2018.01) |
| *G16H 50/20* | (2018.01) |
| *G16H 10/60* | (2018.01) |
| *A61B 5/00* | (2006.01) |
| *G16H 50/30* | (2018.01) |
| *G16H 10/20* | (2018.01) |

(52) U.S. Cl.
CPC ........... *G16H 20/60* (2018.01); *A61B 5/4866* (2013.01); *A61B 5/7246* (2013.01); *A61B 5/7267* (2013.01); *G16H 10/20* (2018.01); *G16H 10/60* (2018.01); *G16H 50/20* (2018.01); *G16H 50/30* (2018.01); *G16H 50/70* (2018.01)

(58) Field of Classification Search
CPC ................ G06H 20/60; G09B 19/0092; A61B 5/14532; G06Q 30/0631; G06Q 10/10; G06Q 50/10

USPC ....................................................... 705/2, 3
See application file for complete search history.

(56) References Cited

U.S. PATENT DOCUMENTS

| | | |
|---|---|---|
| 7,894,849 B2 | 2/2011 | Kass et al. |
| 8,409,104 B2 | 4/2013 | Cobain |

(Continued)

FOREIGN PATENT DOCUMENTS

WO      2018020239      2/2018

OTHER PUBLICATIONS ip.com search, Mar. 14, 2022 (Year: 2022).*

(Continued)

*Primary Examiner* — Dilek B Cobanoglu
(74) *Attorney, Agent, or Firm* — Caldwell Intellectual Property Law

(57) ABSTRACT

A system for modifying a nutrition requirement includes a computing device configured to obtain a user attribute, identify a nutrition requirement as a function of the user attribute, wherein identifying further comprises, receiving a nutrition training set, wherein the nutrition training set relates an aliment to a user attribute, and identifying the nutrition requirement as a function of a nutrition machine-learning process, receive a monitoring element from a monitoring device, modify the nutrition requirement, wherein modifying further comprises, receiving a modification training set, wherein the modification training set relates a monitoring element to a nutrition outcome, and modifying the nutrition requirement as a function of a modification machine-learning process, identify an aliment that fulfills the modified user nutrition requirement, and present an aliment on a display device.

16 Claims, 6 Drawing Sheets

(56) References Cited

U.S. PATENT DOCUMENTS

| | | | |
|---|---|---|---|
| 8,532,938 B2 | 9/2013 | Jung et al. | |
| 8,737,971 B2 | 5/2014 | Van Rooyen | |
| 8,762,167 B2 | 6/2014 | Blander et al. | |
| 8,822,225 B2 | 9/2014 | Gotch et al. | |
| 9,132,219 B2 | 9/2015 | Akonur et al. | |
| 9,183,757 B2 | 11/2015 | Yamada et al. | |
| 9,589,480 B2 | 3/2017 | Ellis | |
| 9,758,839 B2 | 9/2017 | Apte et al. | |
| 9,838,508 B2 | 12/2017 | Salem | |
| 10,068,494 B2* | 9/2018 | Ahmad | G09B 5/02 |
| 10,102,345 B2 | 10/2018 | Yanev et al. | |
| 10,127,361 B2 | 11/2018 | Hyde et al. | |
| 10,133,849 B2 | 11/2018 | Yanev et al. | |
| 10,720,235 B2* | 7/2020 | Leifer | G06F 16/9035 |
| 10,776,856 B2* | 9/2020 | Leifer | G06F 16/9035 |
| 2007/0269557 A1* | 11/2007 | Culver | G09B 19/0092 426/72 |
| 2008/0059342 A1* | 3/2008 | Culver | G06Q 50/10 705/28 |
| 2008/0091705 A1* | 4/2008 | McBride | G06Q 50/10 707/999.102 |
| 2008/0177149 A1 | 7/2008 | Weinert et al. | |
| 2008/0195594 A1 | 8/2008 | Gerjets et al. | |
| 2008/0306763 A1 | 12/2008 | James | |
| 2009/0006127 A1* | 1/2009 | Bahar | G06Q 10/10 705/2 |
| 2010/0098809 A1 | 4/2010 | Bender et al. | |
| 2013/0079612 A1 | 3/2013 | Hunt et al. | |
| 2013/0138447 A1 | 5/2013 | Nova et al. | |
| 2015/0012295 A1 | 1/2015 | Mahoney | |
| 2016/0042152 A1 | 2/2016 | Oran | |
| 2017/0216518 A1 | 8/2017 | Davis et al. | |
| 2018/0032698 A1 | 2/2018 | Lau et al. | |
| 2019/0290172 A1* | 9/2019 | Hadad | A61B 5/14532 |
| 2020/0042865 A1 | 3/2020 | Lee et al. | |

OTHER PUBLICATIONS

Westerman, et al.; Longitudinal analysis of biomarker data from a personalized nutrition platform in healthy subjects; Scientific Reports; Oct. 2, 2018; https://www.nature.com/articles/s41598-018-33008-7.pdf.

Inside Tracker; Who we are; file:///C:/Users/LindseyPowell/Downloads/InsideTracker's%20expert%20team_%20scientists...pdf.

Bald, Eric; The A.I. Diet; https://www.weizmann-usa.org/news-media/in-the-news/the-ai-diet.

Ramachandran, Swaroopini; Mar. 15, 2019; The algorithm to a perfect diet—AI has answers; http://peasonmoss.com/2019/03/15/the-algorithm-to-a-perfect-diet-ai-has-answers/.

VK, Anirudh; 5 AI-Powered fitness startups in India who are using data science to promote healthy lifestyle; https://www.analyticsindiamag.com/5-ai-powered-fitness-startups-in-india-who-are-using-data-science-to-promote-healthylifestyle/.

* cited by examiner

SYSTEM AND METHOD FOR MODIFYING A NUTRITION REQUIREMENT

FIELD OF THE INVENTION

The present invention generally relates to the field of artificial intelligence. In particular, the present invention is directed to a system and method for modifying nutrition requirements.

BACKGROUND

Nutrition requirements are universal for individuals, resulting in poor results for individuals and frustrating individuals. This is further complicated by the overwhelming source of nutrition requirements further confusing and frustrating individuals. The lack of personalized nutrition requirements in the current consumer market has resulted in individuals that fail to obtain the positive results that are possible.

SUMMARY OF THE DISCLOSURE

In an aspect a system for modifying a nutrition requirement includes a computing device, the computing device configured to receive a user attribute, identify a nutrition requirement as a function of the user attribute, wherein identifying further comprises receiving a nutrition training set, the nutrition training set relating at least an aliment and at least a user attribute and using a nutrition machine-learning process, wherein the nutrition machine-learning process is configured using the nutrition training set, receive a monitoring element from a monitoring device, modify the nutrition requirement as a function of the monitoring element, wherein modifying further comprises receiving a modification training set, wherein the modification training set relates a monitoring element and a nutrition outcome, and using a modification machine-learning process, wherein the modification machine-learning process is configured using the modification training set, identify an aliment that fulfills the modified user nutrition requirement, and present the aliment on a display device.

In another aspect a method for modifying a nutrition requirement includes receiving, by a computing device, a user attribute, identifying, by the computing device, a nutrition requirement as a function of the user attribute, wherein identifying further comprises receiving a nutrition training set, the nutrition training set relating at least an aliment and at least a user attribute and using a nutrition machine-learning process, wherein the nutrition machine-learning process is configured using the nutrition training set, receiving, by the computing device, a monitoring element from a monitoring device, modifying, by the computing device, the nutrition requirement as a function of the monitoring element, wherein modifying further comprises receiving a modification training set, wherein the modification training set relates a monitoring element and a nutrition outcome, and using a modification machine-learning process, wherein the modification machine-learning process is configured using the modification training set, identifying, by the computing device, an ailment that fulfills the modified user nutrition requirement, and presenting, by the computing device, the aliment on a display device.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations, and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for modifying a nutrition requirement. In an embodiment this system modifies the nutrition requirement as a function of a user attribute and a monitoring element. Aspects of the present disclosure can be used to modify the nutrition requirement that at least enhances a user attribute as a function of the monitoring element. This is so at least in part, because the system obtains a user attribute from the user, identifies a nutrition requirement, and modifies the nutrition requirement as a function of a monitoring element obtained from a monitoring device. In an embodiment, B. Exemplary embodiments illustrating aspects of the present disclosure are described below in the context of several specific examples.

Figure 1:
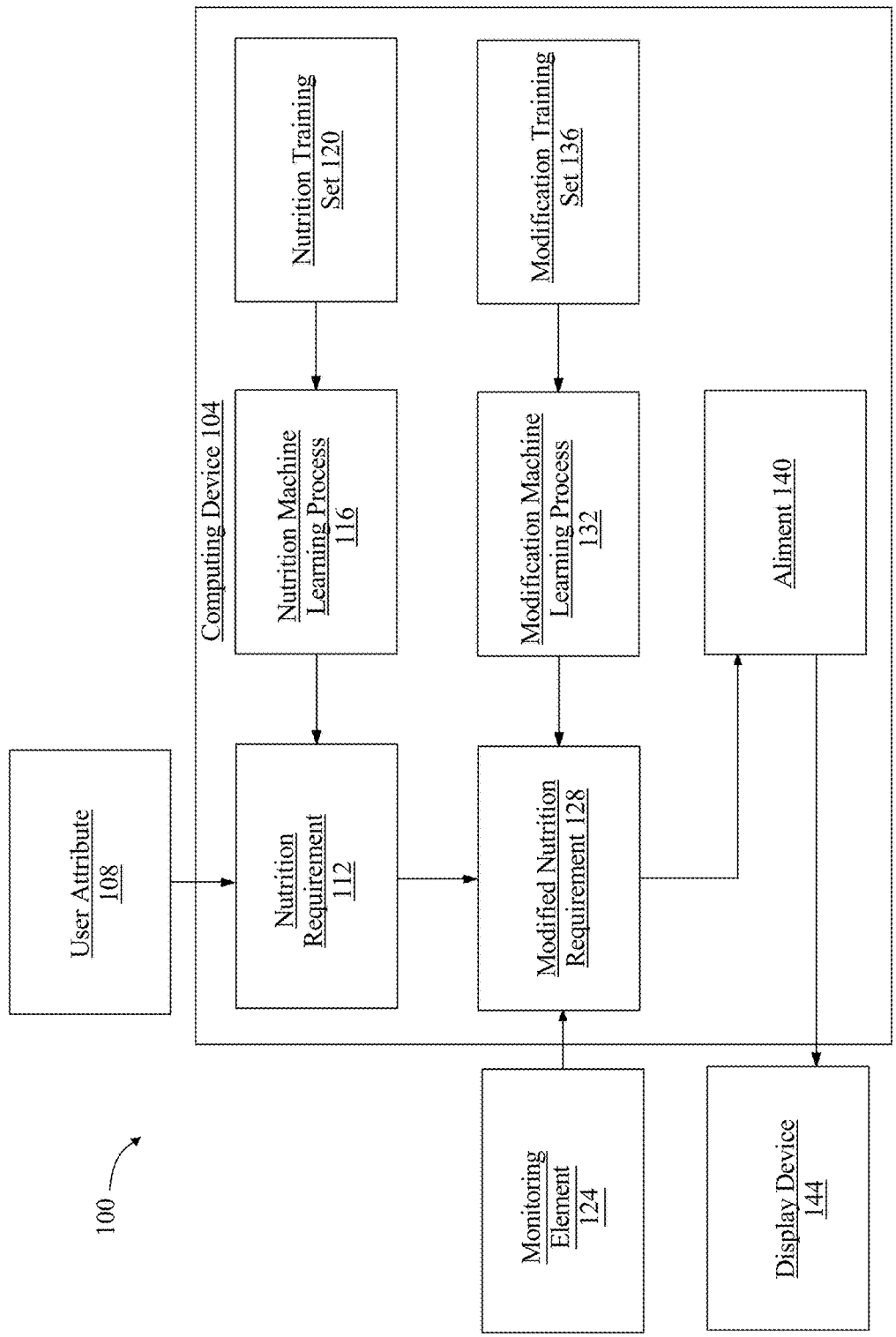
FIG. 1 is a block diagram illustrating an exemplary embodiment of a system for modifying a nutrition requirement.

Referring now to FIG. 1, an exemplary embodiment of a system 100 for modifying a nutrition requirement is illustrated. System includes a computing device 104. Computing device 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Computing device 104 may include a single computing device operating independently, or may include two or more computing device operating in concert, in parallel, sequentially or the like; two or more computing devices may be included together in a single computing device or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Computing device 104 may include but is not limited to, for example, a computing device or cluster of computing devices in a first location and a second computing device or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device, which may operate in parallel, in series, redundantly, or in any other manner used for distribution of tasks or memory between computing devices. Computing device 104 may be implemented using a "shared nothing" architecture in which data is cached at the worker, in an embodiment, this may enable scalability of system 100 and/or computing device.

Computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, computing device 104 is configured to receive a user attribute 108. As used in this disclosure a "user attribute" relates to a characteristic uniquely belonging to a user. User attribute 108 may include, without limitation, particular traits, qualities, behaviors, and/or habits relating to a user. User attribute 108 may be comprised of a medical record, vigor status, and/or health qualifier. As used in this disclosure "vigor status" relates to a qualitative measure of a user health. User vigor status may include without limitation, a user affliction, a user fitness status, a user wellness goal, a user medical goal, or the like thereof. As used in this disclosure a "user affliction" is a list or collection of current or potential ailments and/or diseases, and/or precursor states to such ailments and/or diseases, including but not limited to physical, spiritual, and/or psychological ailments and/or diseases correlating to any resulting impact on the user. In an embodiment a physical ailment or disease may include, without limitation, Influenza, Rhinovirus, Obesity, COVID-19, EEE, CRE, Ebola, Enterovirus D68, Influenza, Hantavirus, Hepatitis A, Hepatitis A, HIV/AIDS, Diabetes (Type I or Type II), Multiple Sclerosis, Chron's Disease, Colitis, Lupus, Rheumatoid Arthritis, Allergies, Asthma, Relapsing Polychondritis, Scleroderma, Liver Disease, Heart Disease, Cancer, and the like thereof. In an embodiment a spiritual ailment or disease may include, without limitation, religious conflicts, chakra blockages, existential crisis, or the like thereof. In an embodiment a psychological ailment or disease may include, without limitation, Alzheimer's, Parkinson's, alcohol or substance abuse disorder, anxiety disorder, ADD, ADHD, bipolar disorder, depression, eating disorder, obsessive-compulsive disorder, opioid use disorder, PTSD, schizophrenia, depersonalization disorder, dissociative amnesia and/or fatigue, anorexia, bulimia, sleep disorders, wake disorders, paraphilic disorders, sexual disorders, child mental disorders, personality disorders, gender dysphoria, depression, and the like thereof. As used in this disclosure a "user fitness status" is an enumeration vector relating a user fitness to a fitness capability. For example, and without limitation, a user fitness status may indicate a user to have a low fitness status, wherein a low fitness status indicates the user to be below average for fitness levels. As used in this disclosure a "user wellness goal" is a set value or metric that a user would like to achieve relating to the user's wellness. For example, and without limitation, a user wellness goal may include increased sleep, enhanced meditation, increase positivity, or the like thereof. As used in this disclosure a "user medical goal" is a set value or metric that a user and/or physician would like the user to achieve to increase overall medical health. For example, and without limitation, a user medical goal may include decrease LDL, lower blood pressure, reduced heart rate, increased lung capacity, increased metabolic rate, or the like thereof. As used in this disclosure a user "health qualifier" is a pre-existing limiting medical or psychological concern. For example, a health qualifier may include a psychological barrier, wherein the psychological barrier is preventing a user from performing a specific action or task.

Still referring to FIG. 1, user attribute 108 may further be comprised of comprised of a user edible history. As used in this disclosure a "user aliment history" is a history of previous aliment selections made by the user. For example, and without limitation, user aliment history may include aliment habits, aliments selected as a function of fitness related activities, aliment preference, calories consumed, and the like thereof. As used in this disclosure "aliment habits" are aliments that are frequently selected by the user. For example, and without limitation, a user may frequently select bacon and eggs as a preference for a breakfast aliment. Aliments selected as a function of fitness activities may include, without limitation, elevated protein aliments, energy supplements, fat-burning supplements, and the like thereof. As used in this disclosure "aliment preference" is a user wish, urge, want, and/or partiality towards a specific aliment. For example, a user may have an aliment preference of sweet aliments as opposed to sour aliments. A user aliment history may include inputs from a food service databank. As used in this disclosure "food service datastore" is a datastore relating the user to previously purchase aliments. For example, and without limitation, a food service databank may include the database GRUBHUB service as provided by GrubHub of Chicago, Ill., the database UBEREATS service as provided by UberEats of San Francisco, Calif., the database RESTOLABS service as provided by RestoLabs of Reno, Nev., the database 9FOLD service as provided by 9Fold Software of New York, N.Y., the database MENUDRIVE service as provided by MenuDrive of Albuquerque, N. Mex., the database SKIP THE COMMISION service as provided by Skipthecommission Online Ordering Systems of Toronto, Canada, the database GLORIA FOOD service as provide by GloriaFood of Bucharest, Romania, the database IMENU360 service as provided by iMenu360 of Winnetka, Ill., the database RESTROAPP service as provided by RestroApp of Iselin, N.J., the database ORDERING.CO service as provided by Ordering.co Berlin, Germany, the database CLOUD WAITRESS service as provided by Cloud Waitress of Sydney, Australia, the database HELLOFRESH service as provided by HelloFresh of Berlin, Germany, the database BLUE APRON service provided by Blue Apron of New York, N.Y., The database TRIFECTA NUTRITION service as provided by Trifecta Nutrition of Sacramento, Calif., the database FRESHLY service as provided by Freshly of New York, N.Y., the database GREEN CHEF service as provided by Green Chef of Boulder, Colo., the database PURPLE CARROT as provided by Purple Carrot of Needham, Mass., the database PEACH DISH as provided by Peach Dish of Atlanta, Ga., the database PLATED service as provided by Plated of New York, N.Y., the database service of HOME CHEF as provided by Home Chef of Chicago, Ill., the database CLEAN EATS KITCHEN service as provided by Clean Eats Kitchen of Myrtle Beach, N.C., the database INSTACART service as provided by Instacart of San Francisco, Calif., the database HUNGRY ROOT service as provided by Hungry Root of New York, N.Y., the database SUNBASKET service as provided by Sunbasket of San Francisco, Calif., the database DAILY HARVEST service as provided by Daily Harvest of New York, N.Y., the database GOBBLE service as provided by Gobble of Palo Alto, Calif., the database SPLENDID SPOON service as provided by Splendid Spoon of New York, N.Y., and the like thereof. A user aliment history may include questionnaire and/or survey. As used in this disclosure a "questionnaire" is an organized list questions, examinations, and/or queries that relate to the user aliment history. For example, and without limitation, a user may be asked how many times a week they consume chocolate and/or deserts. A user aliment history may include history from a databank as a function of a user participation vector. As used in this disclosure a "user participation vector" is a value that relates a user's previous history of participation in nutrition requirements. For example, and without limitation, a participation vector of 20 may be previously stored relating a strong likelihood for a user to maintain a nutrition requirement, while a participation vector of 1 previously stored may relate a low likelihood for a user to maintain a nutrition requirement.

Still referring to FIG. 1, user attribute may be further comprised of user input, wherein the user input includes an element relating to health conditions. As used in this disclosure "user input" is any datum, value, vector, or element entered to computing device 104. A user input may include a user's previous meal selection. As used in this disclosure a "health condition" is the physical or emotional status of the user. A physical status, may include, without limitation, normal, good, well, fatigue, lethargic, tired, disease, sick, ill, or the like thereof. An emotional status of the user may include anger, disgust, fear, happiness, sadness, surprise, neutrality, joy, trust, anticipation, friendship, shame, kindness, pity, indignation, envy, love, suffering, and the like thereof.

With continued reference to FIG. 1, computing device 104 is configured to identify a nutrition requirement 112 as a function of the user attribute. As used in this disclosure a "nutrition requirement" is a required nutrient the user needs to consume in order to enhance and/or aid the user attribute. Nutrition requirement may be comprised of nutrients including, but not limited to, carbohydrates, complex carbohydrates, lipids, fatty acids, steroids, cholesterols, proteins, amino acids branched chain amino acids, vitamins, minerals, electrolytes, and the like thereof. For example a nutrition requirement may include, without limitation, 64 grams of protein, 30 grams of fiber, 900 mg of vitamin A, 1.2 mg of Thiamin, 1.3 mg of riboflavin, 16 mg of niacin, 1.3 mg of vitamin B6, 2.4 mg of vitamin B12, 500 mg of folate, 45 mg of vitamin C, 1 gram of calcium, 150 mg of iodine, 8 mg of iron, 500 mg or magnesium, 3.8 grams of potassium, 460 mg of sodium, 14 mg of zinc, and 200 mg of carbohydrates. Nutrition requirement is identified as a function of a nutrition machine-learning process 116. As used in this disclosure a "nutrition machine-learning process" is a machine-learning process that automatedly uses training data and/or a training set to generate an algorithm that will be performed by a computing device and/or module to produce outputs given data provided as inputs; this is in contrast to a non-machine-learning software program where the commands to be executed are determined in advance by a user and written in a programming language. Nutrition machine-learning process 116 may consist of any supervised, unsupervised, or reinforcement machine-learning process that computing system 104 may or may not use in the determination of nutrition requirement 112. Nutrition machine-learning process 112 may include, without limitation, machine-learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, nutrition machine-learning process 116 may be calculated as a function of a nutrition training set 120. As used in this disclosure "nutrition training set" is a training set that correlates at least an aliment to a user attribute, wherein a user attribute is described above. For example, a user attribute may include, without limitation, fever, influenza, vomiting, nausea, headache, chills, numbness, and the like thereof. As used in this disclosure an "aliment" is a source of nutrition that may be consumed by a user such that the user may absorb the nutrients from the source. For example and without limitation, an aliment may include legumes, plants, fungi, nuts, seeds, breads, dairy, eggs, meat, cereals, rice, seafood, desserts, dried foods, dumplings, pies, noodles, salads, stews, soups, sauces, sandwiches, and the like thereof. As a non-limiting example nutrition training set 120 may relate a user attribute of lethargy with coffee beans and or bananas, wherein coffee beans provide the nourishment of caffeine to increase energy levels and bananas provide the nourishment of potassium to also increase energy levels. Additionally or alternatively, nutrition machine-learning process 116 may be generated as a function of a classifier, wherein the classifier may receive the user affliction of a plurality of user afflictions and output one or more aliments that are related to at least one or more user afflictions. As used in this disclosure a "classifier" is a machine-learning model, such as a mathematical model, neural net, or program generated by a machine-learning algorithm known as a "classification algorithm," as described below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Computing device 104 and/or another device may generate a classifier using a classification algorithm, defined as a process whereby a computing device 104 derives a classifier from training data. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. For example, and without limitation, a classifier may receive an input of depressed, wherein an aliment of chocolate may be outputted as chocolate may provide increased levels of dopamine and may reduce the effects of dopamine.

Still referring to FIG. 1, computing device 104 may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A) P(A)+P(B)$, where P(AB) is the probability of hypothesis A given data B also known as posterior probability; P(B/A) is the probability of data B given that the hypothesis A was true; P(A) is the probability of hypothesis A being true regardless of data also known as prior probability of A; and P(B) is the probability of the data regardless of the hypothesis. A naïve Bayes algorithm may be generated by first transforming training data into a frequency table. Computing device 104 may then calculate a likelihood table by calculating probabilities of different data entries and classification labels. Computing device 104 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 1, computing device 104 may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 1, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm: $l=\sqrt{\Sigma_{i=0}^{n} a_i^2}$, where a is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

Still referring to FIG. 1 computing device 104 is configured to receive a monitoring element 124 from a monitoring device. As used in this disclosure a "monitoring element" is a sign, symptom, element, or quality that relates to a user. For instance, monitoring element 124 may include, without limitation, heart rate, calories burned, steps walked, blood pressure, biochemicals detected, time spent exercising, seizures, physical strain, or the like thereof. As a further non-limiting example, monitoring element 124 may include mood quality, anxiety levels, sleep quality, or the like thereof. As used in this disclosure "monitoring device" is an electronic device that is worn on the person of a user, such as without limitation close to and/or on the surface of the skin, wherein the device can detect, analyze, and transmit information concerning a body signal such as a vital sign, and/or ambient datum, wherein allowing immediate biofeedback to be sent to the user wearing the device. For example and without limitation, a monitoring device may include, without limitation, any device that further collects, stores, and analyzes data associated with monitoring elements. As a further non-limiting example, a monitoring device may consist of near-body electronics, on-body electronics, in-body electronics, electronic textiles, smart watches, smart glasses, smart clothing, fitness trackers, body sensors, wearable cameras, head-mounted displays, body worn cameras, Bluetooth headsets, wristbands, smart garments, chest straps, sports watches, fitness monitors, and the like thereof. As a further non-limiting example, a monitoring device may include earphones, earbuds, headsets, bras, suits, jackets, trousers, shirts, pants, socks, bracelets, necklaces, brooches, rings, jewelry, AR HMDs, VR HMDs, exoskeletons, location trackers, and gesture control wearables. As a further non-limiting example, a monitoring device may consist of, without limitation an Apple watch, Galaxy watch, FitBit Sense, Fossil Gen 5, Tag Heuer Connected, Garmin Instinct, and the like thereof.

Still referring to FIG. 1, computing device 104 is configured to modify nutrition requirement 112 such that a modified nutrition requirement 128 results as a function of monitoring element 124. As used in this disclosure "modified nutrition requirement" is an altered nutritional necessity that is generated as a function of the monitoring element. For example a nutrition requirement of 120 grams of protein, 15 grams of fiber, 800 mg of vitamin A, 3.4 mg of Thiamin, 6.8 mg of riboflavin, 20 mg of niacin, 5 mg of vitamin B6, 0.4 mg of vitamin B12, 300 mg of folate, 21 mg of vitamin C, 5 grams of calcium, 100 mg of iodine, 9 mg of iron, 150 mg or magnesium, 5 grams of potassium, 350 mg of sodium, 16 mg of zinc, and 500 mg of carbohydrates, wherein a monitoring element of high blood sugar may be obtained, resulting in a modified nutrition requirement of 20 mg of carbohydrates instead of the 500 mg previously identified. Modified nutrition requirement 128 is generated as a function of a modification machine-learning process 132. As used in this disclosure "modification machine-learning process" is a machine-learning process that automatedly uses training data and/or a training set to generate an algorithm that will be performed by a computing device and/or module to produce outputs given data provided as inputs; this is in contrast to a non-machine-learning software program where the commands to be executed are determined in advance by a user and written in a programming language. Modification machine-learning process 132 may consist of any supervised, unsupervised, or reinforcement machine-learning process that computing system 104 may or may not use in the determination of modified nutrition requirement 128. Modification machine-learning process 132 may include, without limitation, machine-learning processes such as simple linear regression, multiple linear regression, polynomial regression, support vector regression, ridge regression, lasso regression, elasticnet regression, decision tree regression, random forest regression, logistic regression, logistic classification, K-nearest neighbors, support vector machines, kernel support vector machines, naïve bayes, decision tree classification, random forest classification, K-means clustering, hierarchical clustering, dimensionality reduction, principal component analysis, linear discriminant analysis, kernel principal component analysis, Q-learning, State Action Reward State Action (SARSA), Deep-Q network, Markov decision processes, Deep Deterministic Policy Gradient (DDPG), or the like thereof.

Still referring to FIG. 1, modification machine-learning process 132 Is generated as a function of a modification training set 136. As used in this disclosure a "modification training set" relates at least a monitoring element with a nutrition outcome. As used in this disclosure a "monitoring element" is an element relating to one or more human physiological statuses, wherein human physiological statuses may include heartbeat, blood pressure, body temperature, electrocardiograms, arrhythmias, cancerous indicators, body fat composition, or the like thereof. As a non-limiting example, monitoring elements may include data collected from using one or more pressure sensors, humidity sensors, position sensors, piezo film sensors, force sensors, temperature sensors, optical sensors, or the like thereof. As a further non-limiting example monitoring elements may include data collected from using X-ray absorptiometry, hydrostatic weighing, air displacement plethysmography, bioelectrical impedance analysis, bioimpedance spectroscopy, electrical impedance myograph, 3-D scanners, and multi-compartment models. As used in this disclosure a "nutrition outcome" is a resulting nutrition deficiency associated with the monitoring element. For example, and without limitation a nutrition outcome may include a monitoring element of decreased red blood cell count, wherein the nutrition outcome may correlate to low concentrations of concentrations of iron. As a further non-limiting a monitoring element of high blood pressure, may correlate to an increased saturated fat. As a further non-limiting example a monitoring element of decreased sleep may correlate to lower concentrations of caffeine and or niacin in a user.

Still referring to FIG. 1, computing device 104 is configured to identify an aliment 140 that fulfills modified nutrition requirement 128, wherein an aliment is discussed in detail above. As a non-limiting example, computing device 104 may identify an aliment of spinach as a function of a modified nutrition requirement of low iron. Computing device 104 may further hierarchically sort aliments. As used in this disclosure a "sorted list" is an ordered collection of data elements for which an order of presentation is defined according to ascending or descending values of a quantitative or other textual field associated with each element in the ordered collection. Computing device 104 may accomplish this, without limitation, by determining a nourishment value corresponding to the modified nutrition requirement. As used in this disclosure "nourishment value" is a quantitative value associated with the nutrients contained in each potential aliment. As a non-limiting example a nourishment value for salmon may be 90 for omega-3-fatty acids, 30 for protein, 2 for saturated fat, and 0.1 for carbohydrates. Computing device 104 may utilize an individual nourishment value or a combination of nourishment values to determine the sorted aliment list.

Still referring to FIG. 1, computing device 104 may create a distance metric from the nourishment value to a candidate aliment of a plurality of candidate aliments and select at least an aliment that minimizes the distance. As used in this disclosure, a "distance metric" is a quantitative value indicating a degree of similarity of a set of data values to another set of data values. For instance, and without limitation, combinations of nourishment values associated with each candidate aliment of a plurality of candidate aliments may be represented a vector. Each vector may be represented, without limitation, as an n-tuple of values, where n is at least two values. Each value of n-tuple of values may represent a measurement or other quantitative value associated with a given category of data, or attribute, such as a nutrients, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. A non-limiting distance metric may include a degree of vector similarity. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent, for instance as measured using cosine similarity; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm: $l = \sqrt{\sum_{i=0}^{n} a_i^2}$, where a is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values. As a non-limiting illustration, nourishment values from candidate aliments, and/or one or more subsets thereof, may be represented using a vector or other data structure, and nutrients provided by each candidate aliment of a plurality of candidate aliments may be represented by a like data structure, such as another vector; a distance metric comparing the two data structures may then be calculated and compared to distance metrics calculations to find a minimal distance metric calculation and/or a set of minimal distance metric calculations. A set of minimal distance metric calculations may be a set of distance metric calculations less than a preconfigured threshold distance from data structure representing target nutrients. Preconfigured threshold may be set by one or more expert users and/or determined statistically, for instance by finding a top quartile and/or number of percentiles of proximity in a series of distance metric determinations over time for user, at one time for a plurality of users, and/or over time for a plurality of users. Plurality of users may include a plurality of users selected by a user classifier, which may classify user to a plurality of users having similar physiological data and/or user data; implementation of a user classifier may be performed, without limitation, as described in U.S. Nonprovisional application Ser. No. 16/865,740, filed on May 4, 2020 and entitled "METHODS AND SYSTEMS FOR SYSTEM FOR NUTRITIONAL RECOMMENDATION USING ARTIFICIAL INTELLIGENCE ANALYSIS OF IMMUNE IMPACTS," the entirety of which is incorporated herein by reference. In an embodiment, a distance metric may include a measurement of an optimization of one or more factors that include carbohydrates, fats, and/or protein.

Still referring to FIG. 1, computing device 104 is configured to present aliment 140 on a display device 144. As used in this disclosure a "display device" is an output device for presentation of information in visual or tactile form. As a non-limiting example a display device may include liquid crystal display (LCD), a cathode ray tube (CRT), a plasma display, a light emitting diode (LED) display, an electroluminescent (ELD) display, a quantum dot (QLED) display, and the like thereof in any combination. Computing device 104 may display an aliment and/or a sorted list of aliments for the user.

Figure 2:
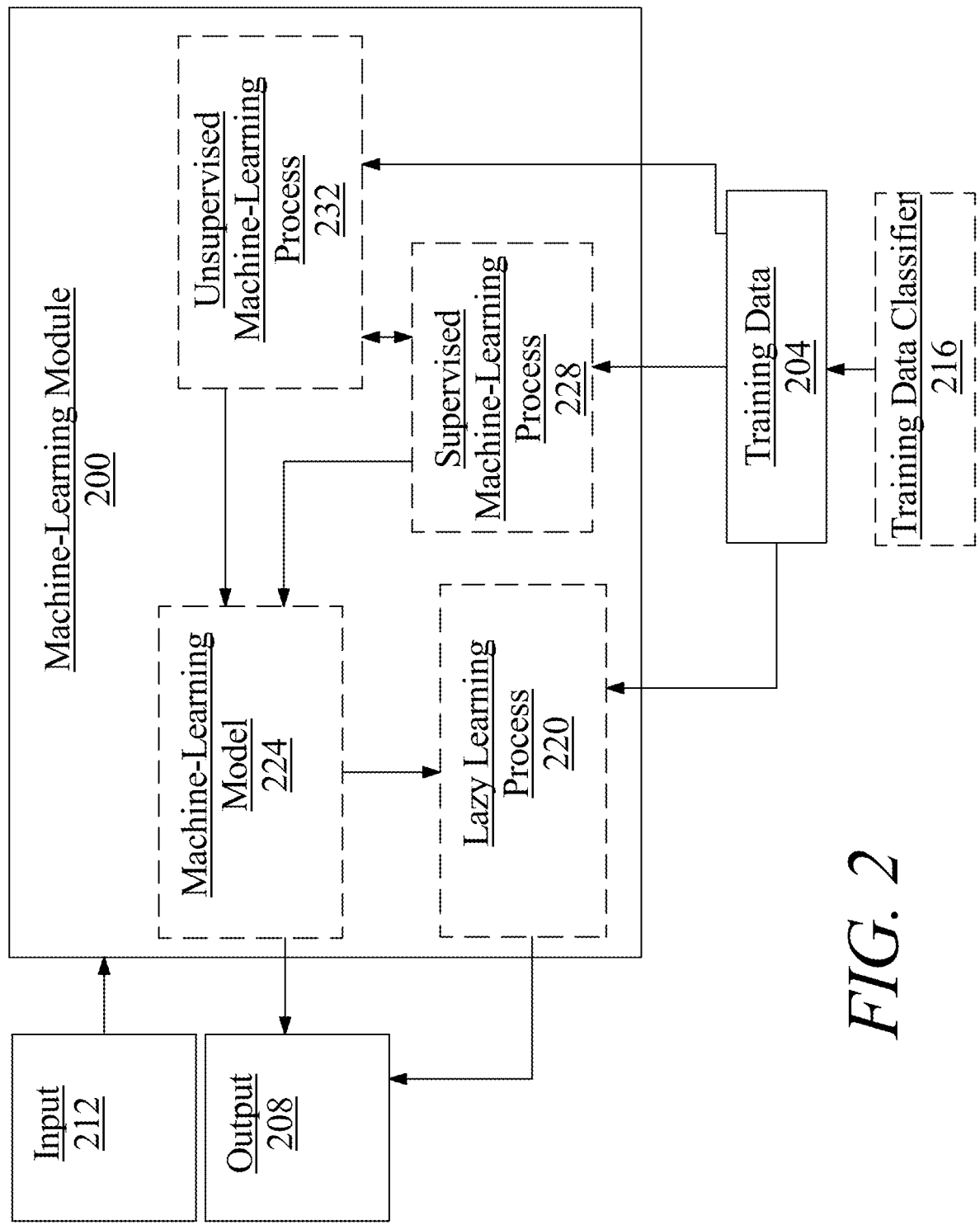
FIG. 2 is a block diagram of an exemplary embodiment of a machine-learning module.

Referring now to FIG. 2, an exemplary embodiment of a machine-learning module 200 that may perform one or more machine-learning processes as described in this disclosure is illustrated. Machine-learning module may perform determinations, classification, and/or analysis steps, methods, processes, or the like as described in this disclosure using machine-learning processes. A "machine-learning process," as used in this disclosure, is a process that automatedly uses training data 204 to generate an algorithm that will be performed by a computing device/module to produce outputs 208 given data provided as inputs 212; this is in contrast to a non-machine-learning software program where the commands to be executed are determined in advance by a user and written in a programming language.

Still referring to FIG. 2, "training data," as used herein, is data containing correlations that a machine-learning process may use to model relationships between two or more categories of data elements. For instance, and without limitation, training data 204 may include a plurality of data entries, each entry representing a set of data elements that were recorded, received, and/or generated together; data elements may be correlated by shared existence in a given data entry, by proximity in a given data entry, or the like. Multiple data entries in training data 204 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 204 according to various correlations; correlations may indicate causative and/or predictive links between categories of data elements, which may be modeled as relationships such as mathematical relationships by machine-learning processes as described in further detail below. Training data 204 may be formatted and/or organized by categories of data elements, for instance by associating data elements with one or more descriptors corresponding to categories of data elements. As a non-limiting example, training data 204 may include data entered in standardized forms by persons or processes, such that entry of a given data element in a given field in a form may be mapped to one or more descriptors of categories. Elements in training data 204 may be linked to descriptors of categories by tags, tokens, or other data elements; for instance, and without limitation, training data 204 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 2, training data 204 may include one or more elements that are not categorized; that is, training data 204 may not be formatted or contain descriptors for some elements of data. Machine-learning algorithms and/or other processes may sort training data 204 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 204 to be made applicable for two or more distinct machine-learning algorithms as described in further detail below. Training data 204 used by machine-learning module 200 may correlate any input data as described in this disclosure to any output data as described in this disclosure. As a non-limiting illustrative example a user attribute of lethargic may be used as an input, wherein an output may be a nutrition requirement of caffeine.

Further referring to FIG. 2, training data may be filtered, sorted, and/or selected using one or more supervised and/or unsupervised machine-learning processes and/or models as described in further detail below; such models may include without limitation a training data classifier 216. Training data classifier 216 may include a "classifier," which as used in this disclosure is a machine-learning model as defined below, such as a mathematical model, neural net, or program generated by a machine-learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. Machine-learning module 200 may generate a classifier using a classification algorithm, defined as a process whereby a computing device and/or any module and/or component operating thereon derives a classifier from training data 204. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 216 may classify elements of training data to sub-populations of emotional qualifiers, such as aliments that are in a sub-population of energetic, sad, angry, depressed, or the like thereof.

Still referring to FIG. 2, machine-learning module 200 may be configured to perform a lazy-learning process 220 and/or protocol, which may alternatively be referred to as a "lazy loading" or "call-when-needed" process and/or protocol, may be a process whereby machine-learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 204. Heuristic may include selecting some number of highest-ranking associations and/or training data 204 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 2, machine-learning processes as described in this disclosure may be used to generate machine-learning models 224. A "machine-learning model," as used in this disclosure, is a mathematical and/or algorithmic representation of a relationship between inputs and outputs, as generated using any machine-learning process including without limitation any process as described above, and stored in memory; an input is submitted to a machine-learning model 224 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 224 may be generated by creating an artificial neural network, such as a convolutional neural network comprising an input layer of nodes, one or more intermediate layers, and an output layer of nodes. Connections between nodes may be created via the process of "training" the network, in which elements from a training data 204 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 2, machine-learning algorithms may include at least a supervised machine-learning process 228. At least a supervised machine-learning process 228, as defined herein, include algorithms that receive a training set relating a number of inputs to a number of outputs, and seek to find one or more mathematical relations relating inputs to outputs, where each of the one or more mathematical relations is optimal according to some criterion specified to the algorithm using some scoring function. For instance, a supervised learning algorithm may include insomnia as described above as inputs, nutrition plans with aliments containing high levels of tryptophan as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 204. Persons skilled in the art, upon reviewing the entirety of this disclosure, will be aware of various possible variations of at least a supervised machine-learning process 228 that may be used to determine relation between inputs and outputs. Supervised machine-learning processes may include classification algorithms as defined above.

Further referring to FIG. 2, machine-learning processes may include at least an unsupervised machine-learning processes 232. An unsupervised machine-learning process, as used herein, is a process that derives inferences in datasets without regard to labels; as a result, an unsupervised machine-learning process may be free to discover any structure, relationship, and/or correlation provided in the data. Unsupervised processes may not require a response variable; unsupervised processes may be used to find interesting patterns and/or inferences between variables, to determine a degree of correlation between two or more variables, or the like.

Still referring to FIG. 2, machine-learning module 200 may be designed and configured to create a machine-learning model 224 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 2, machine-learning algorithms may include, without limitation, linear discriminant analysis. Machine-learning algorithm may include quadratic discriminate analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized tress, AdaBoost, gradient tree boosting, and/or voting classifier methods. Machine-learning algorithms may include neural net algorithms, including convolutional neural net processes.

Figure 3:
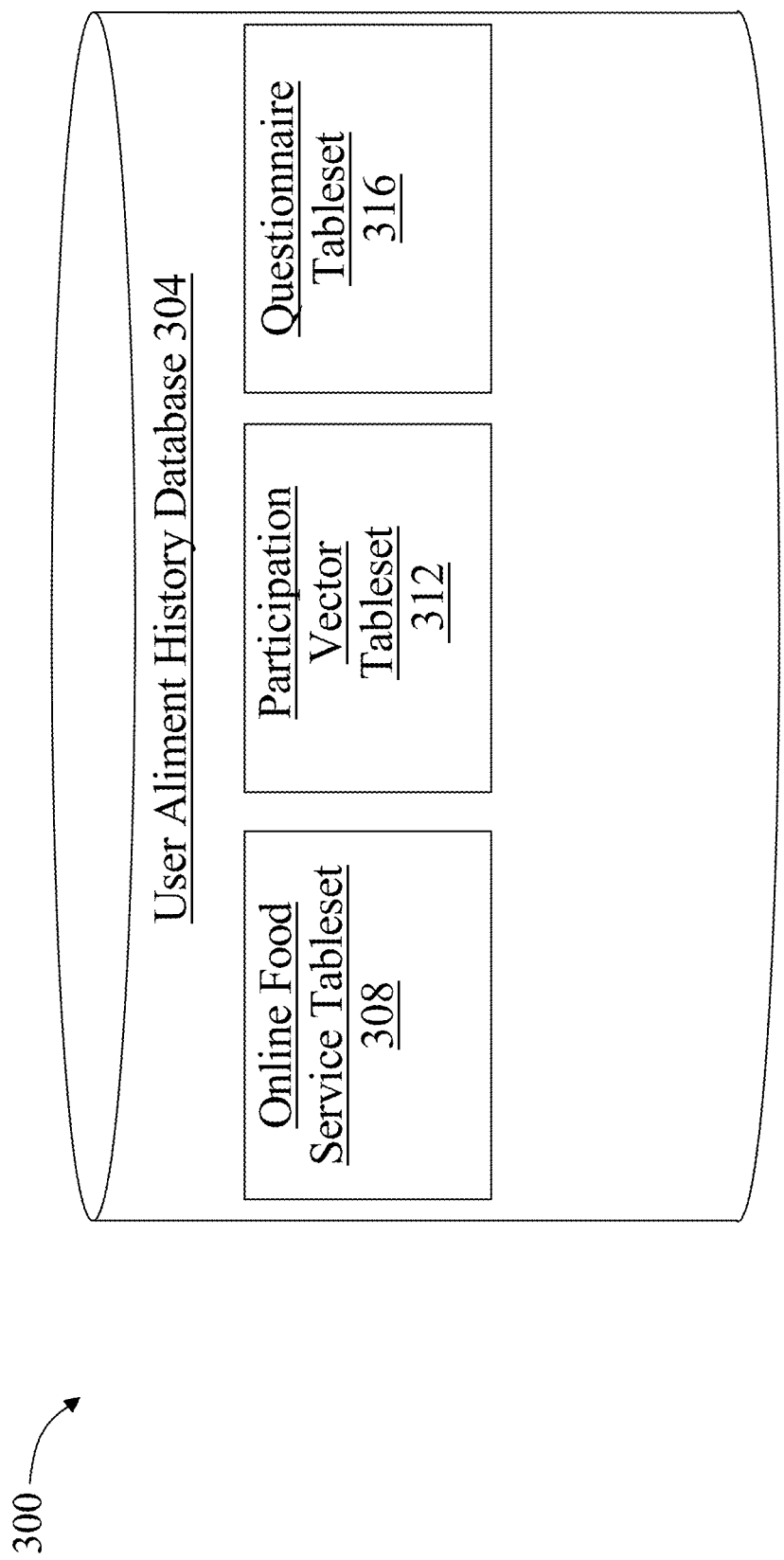
FIG. 3 is a block diagram of an exemplary embodiment of a user edible history database.

Referring now to FIG. 3, an exemplary embodiment of 300 a user aliment history database 304 according to an embodiment of the invention is illustrated. Aliment history database 304 may be implemented, without limitation, as a relational database, a key-value retrieval database such as a NOSQL database, or any other format or structure for use as a database that a person skilled in the art would recognize as suitable upon review of the entirety of this disclosure. Database may alternatively or additionally be implemented using a distributed data storage protocol and/or data structure, such as a distributed hash table or the like. Database may include a plurality of data entries and/or records as described above. Data entries in a database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in a database may store, retrieve, organize, and/or reflect data and/or records as used herein, as well as categories and/or populations of data consistently with this disclosure. User aliment history database may 304 may include one or more tables, including without limitation, an online food service table set 308; online food service tableset 308 may include online food service providers that at least provide an aliment or combination of aliments delivered to a user. As a non-limiting example online food service tableset may include, without limitation, UberEats, Instacart, Jet.com, Drizzly, Blue Apron, or the like thereof. User aliment history database 304 may include a participation vector tableset 312. Participation vector tableset 312 may include previous nutrition requirements that a user has participated in and how effective the nutrition requirement was. As a non-limiting example, participation vector tableset may indicate a user has low participation on diet plans such as weight watchers and/or the Atkins diet, while a user has a high participation in diet plans associated with increased protein such as the Keto-diet or paleo diet. User aliment history databased may include a questionnaire tableset 316. Questionnaire tableset may indicate a user's previous responses to questions associated with preferences, wants, needs, urges, wishes, or partiality towards aliments and/or aliment nutrition.

Figure 4:
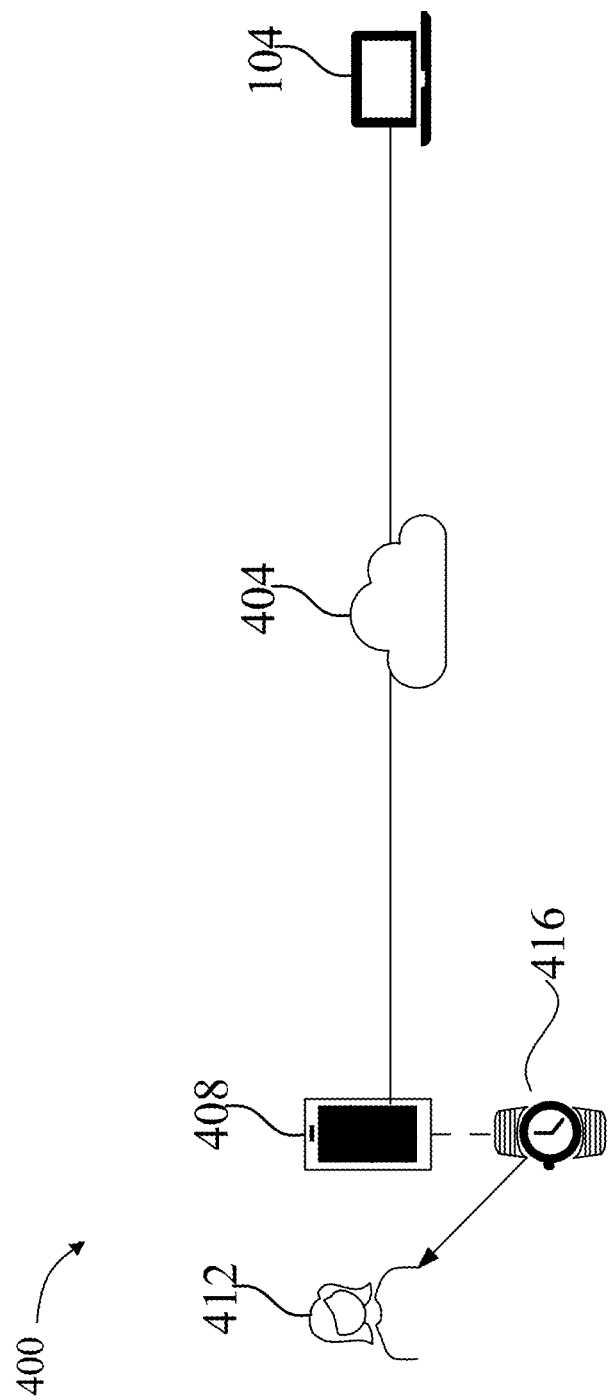
FIG. 4 is a schematic diagram of a system for modifying a nutrition requirement using a monitoring device.

Referring now to FIG. 4, an exemplary embodiment of a schematic for modifying a nutrition requirement using a monitoring device. Computing device 104 is configured to initiate a communication channel interface 404 between computing device 104 and a client device operated by a human subject. A "human subject," as used in this disclosure, is a person using and/or operating a client device. A "communication channel interface," as used in this disclosure, is a communication medium within an interface. Communication channel interface 404 may include an application, script, and/or program capable of providing a means of communication between at least two parties, including any oral and/or written forms of communication. Communication channel interface 404 may allow computing device 104 to interface with electronic devices through graphical icons, audio indicators including primary notation, text-based user interfaces, typed command labels, text navigation, and the like. Communication channel interface 404 may include slides or other commands that may allow a user to select one or more options. Communication channel interface 404 may include free form textual entries, where a user may type in a response and/or message. Communication channel interface 404 includes a display interface. A display interface includes a form or other graphical element having display fields, where one or more elements of information may be displayed. A display interface may display data output fields including text, images, or the like containing one or more messages. Communication channel interface 404 may include data input fields such as text entry windows, drop-down lists, buttons, checkboxes, radio buttons, sliders, links, or any other data input interface that may capture user interaction as may occur to persons skilled in the art upon reviewing the entirety of this disclosure. Communication channel interface 404 may be provided, without limitation, using a web browser, a native application, a mobile application, and the like.

With continued reference to FIG. 4, computing device 104 initiates communication channel interface 404 with a client device 408. A "client device," as used in this disclosure, is a second computing device, including for example a mobile device such as a smartphone, tablet, laptop, desktop, and/or any other type of device suitable for use as computing device. Client device 408 is operated by a human subject 412; human subject 412 may include a person operating a client device. Computing device 104 may initiate communication channel interface 404 using any network methodology as described herein. In an embodiment, a communication channel interface may be utilized to facilitate communications between a client device operated by a human subject, and computing device which may be operated by a user; user may include a secondary human subject that may provide advice and/or monitor a human subject's progress. For example, client device 408 may be operated by a 30-year-old male who is in communication with an informed advisor operating computing device. In yet another non-limiting example, client device may be operated by a first member of a fitness group, and computing device may be operated by a second member of the fitness group, whereby communication channel interface may be utilized to facilitate fitness group meetings and secure communications between members of the fitness group.

With continued reference to FIG. 4, communication channel interface 404 includes a monitoring device 416, wherein a "monitoring device," relates information regarding a physiological status that pertains to client 412, such that a modified nutrition requirement may be identified. Monitoring device 416 may be further comprised, but is not limited to, a camera, a video camera, a mobile device, a recording device, a sensor and/or visual capture device, and the like. In an embodiment, a monitoring device may be located within client device, client clothing, client jewelry, client accessories, and the like thereof.

Figure 5:
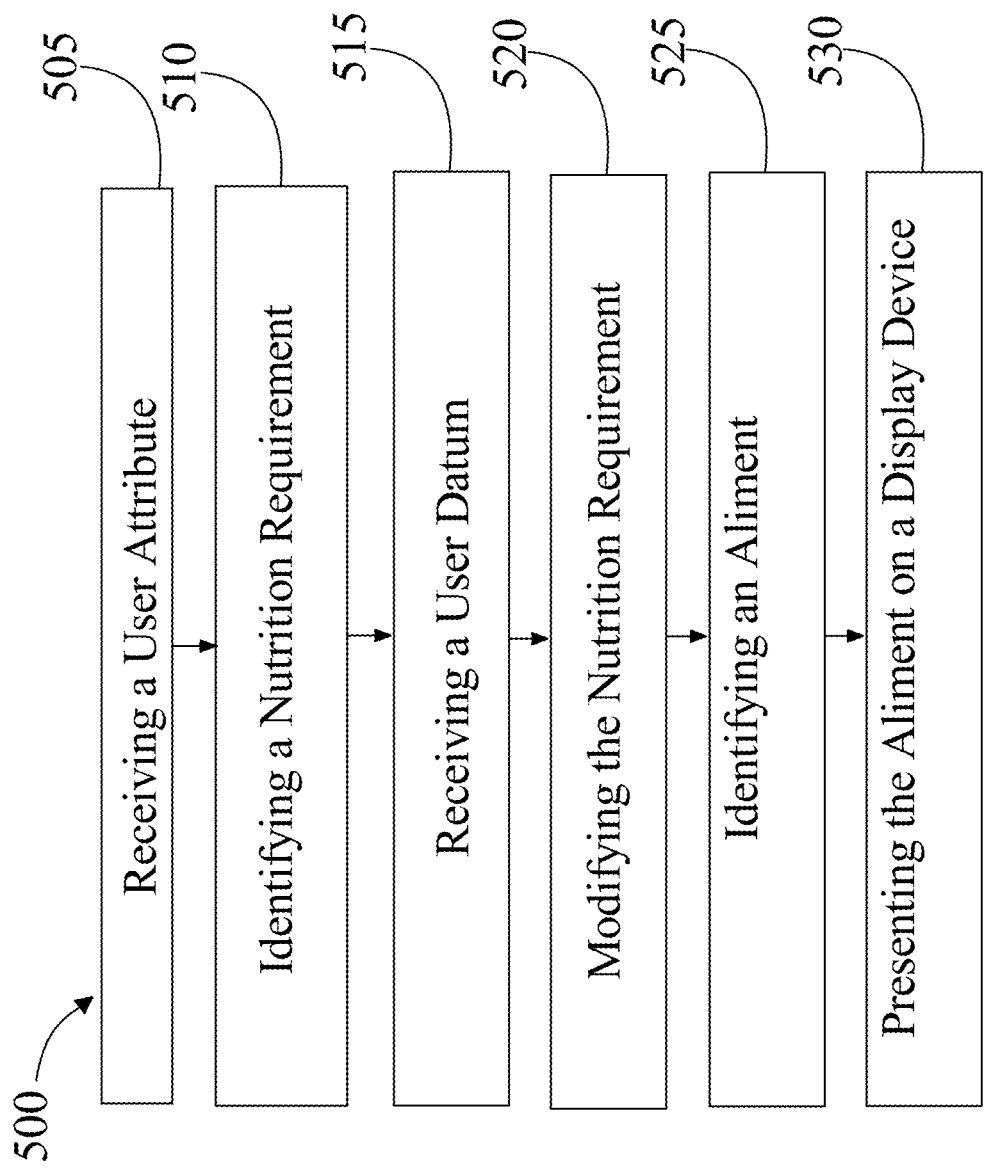
FIG. 5 is process flow diagram illustrating an exemplary embodiment of a method of modifying a nutrition requirement.

Now referring to FIG. 5, an exemplary embodiment of a method 500 of modifying a nutrition requirement. At step 505 a computing device 104 receives a user attribute 108. User Attribute 108 includes any of the user attribute 108 as described above in reference to FIGS. 1-3. User attribute 108 may include a characteristic uniquely belonging to the user. As a non-limiting example user attribute 108 may include particular traits, qualities, behaviors, habits relating to a user, medical records, vigor statuses, health qualifiers, or the like thereof. For instance, and without limitation, a user attribute may include a previous diagnosis of COVID-19. As a further non-limiting example a user status may include a previous enjoyment of a keto diet.

Still referring to FIG. 5, at step 510, computing device 104 identifies a nutrition requirement 112. Nutrition requirement 112 includes any of the nutrition requirement 112 as described above in reference to FIGS. 1-3. Nutrition requirement 112 may include any necessary nutrients required as a function of a user attribute. For instance, and without limitation, a nutrition requirement of omega-3-fatty acids may be required for the user attribute of ischemic heart disease. Computing device 104 may identify nutrition requirement 112 as a function of a nutrition machine-learning process 116. Nutrition machine-learning process 116 includes any of the nutrition machine-learning process 116 as described above, in reference to FIGS. 1-3. For instance, and without limitation, nutrition machine-learning process 116 may include a supervised machine-learning process or an unsupervised machine-learning process. Nutrition machine-learning process 1116 may include a classification process, such as for example naïve Bayes, k-nearest neighbor, decision tree, and/or random forest. Classification processes include any of the classification processes as described above in reference to FIGS. 1-3. Nutrition machine-learning process 116 may be configured using a nutrition training set 120. Nutrition training set 120 includes any of the nutrition training set 120 as described above in reference to FIGS. 1-3. Nutrition training set 120 may include, without limitation aliment correlating to a user attribute, wherein a user attribute is described above. As a non-limiting example nutrition training set 120 may relate a user attribute of overstimulation with melatonin, wherein melatonin reduces the energy levels of a user.

Still referring to FIG. 5, at step 515, computing device 104 receives a monitoring element 124. Monitoring element 124 includes any of the monitoring element 124 as described above in reference to FIGS. 1-3. For instance monitoring element 124 may include heartbeat, temperature, respiratory volume, respiratory rate, blood pressure, movement, bio-impedance, and the like thereof. Monitoring element 124 may be received as a function of a monitoring device. A monitoring device includes any of the monitoring device as described above in reference to FIGS. 1-3. For instance, and without limitation, a monitoring device may include a device or fabric that a user maintains in close proximity to the user, such as a clothing, jewelry, or accessory such that the device can relate monitoring element 124 to computing device 104.

Still referring to FIG. 5, at step 520, computing device 104 modifies nutrition requirement 112, resulting in a modified nutrition requirement 128. Modified nutrition requirement 128 includes any of the modified nutrition requirement 128 as described above, in reference to FIGS. 1-3. Modified nutrition requirement 128 may include, without limitation, an updated nutritional demand as a function of monitoring element 124. For instance, and without limitation modified nutrition requirement 128 may include an updated protein consumption as a result of a monitoring element relating to anemia. Modified nutrition requirement 128 is generated as a function of a modification machine-learning process 132. Modification machine-learning process 132 Includes any of the modification machine-learning process 132 As described above, in reference to FIGS. 1-3. For instance, and without limitation, modified machine-learning process 132 may include a supervised machine-learning process or an unsupervised machine-learning process. Modification machine-learning process 1132 may include a classification process, such as for example naïve Bayes, k-nearest neighbor, decision tree, and/or random forest. Classification processes include any of the classification processes as described above in reference to FIGS. 1-3. Modification machine-learning process 132 may be configured using a modification training set 136. Modification training set 136 includes any of the modification training set 136 as described above in reference to FIGS. 1-3. Modification training set 136 may include, without limitation at least a monitoring element that relates to a nutrition outcome, wherein a monitoring element is an element relating one or more human physiological statuses and a nutrition outcome is a resulting nutrition deficiency that relates to a monitoring element. For instance and without limitation, a monitoring element of rapid heart rate may relate to a nutrition outcome of decreased protein in the user.

Still referring to FIG. 5, at step 525, computing device 104 identifies an aliment 140. Aliment 140 includes any of the aliment 140 as described above in reference to FIGS. 1-3. Aliment 140 may include, without limitation, a source of nutrition to be consumed by a user such that the user obtains the nutrients from the source. For instance, and without limitation, an aliment may include meats, eggs, milk, fruits, vegetables, and the like thereof.

Still referring to FIG. 5, at step 530, computing device 104 presents aliment 140 on a display device 144. As used in this disclosure display device 144 includes any of the display device 144 as described above, in reference to FIGS. 1-3. Display device 144 may include, without limitation any monitor, screen, or window capable of depicting information. Display device 144 may include televisions, computer screens, mobile screens, projectors, and the like thereof.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 6:
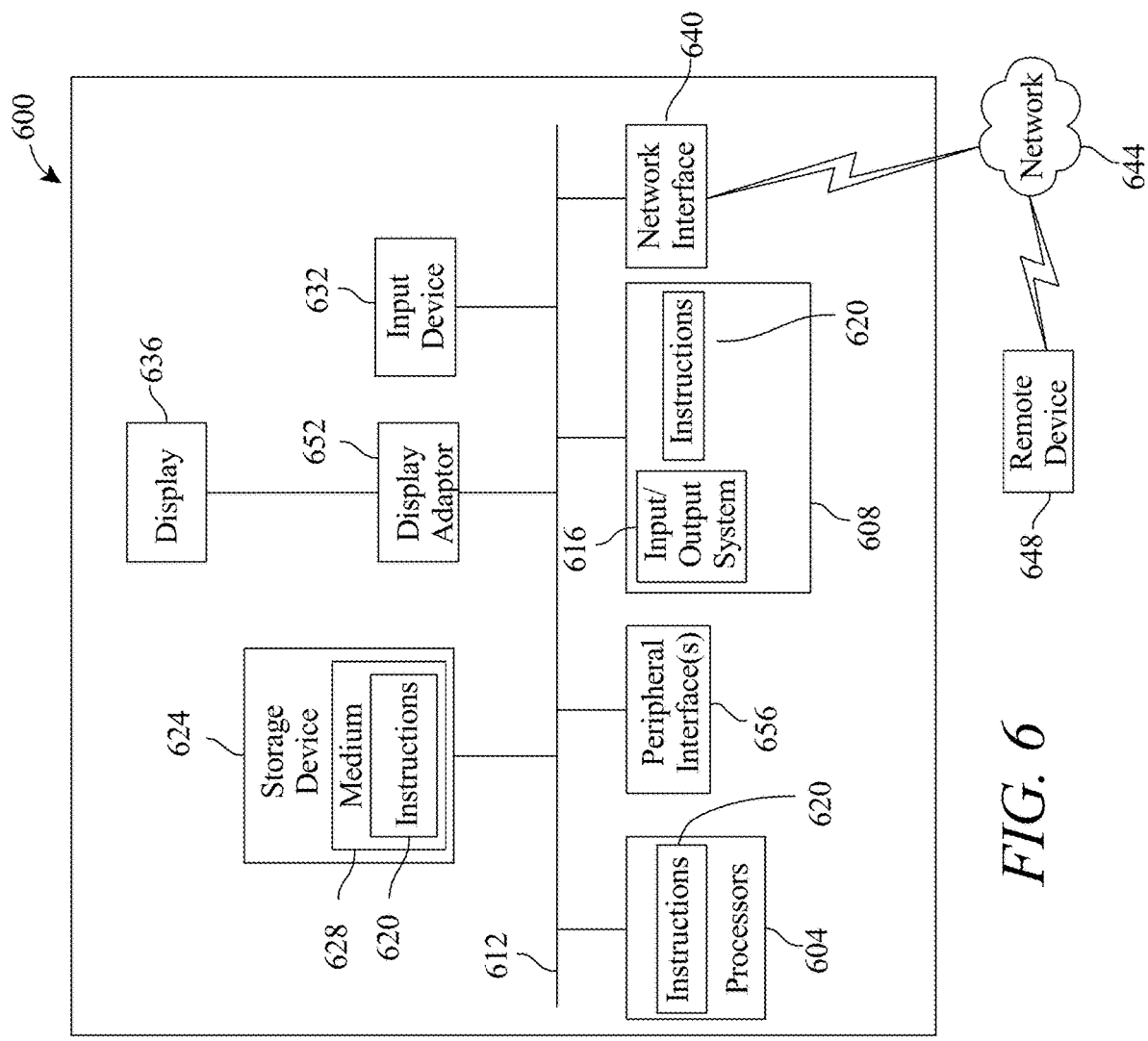
FIG. 6 is a block diagram of a computing system that can be used to implement any one or more of the methodologies disclosed herein and any one or more portions thereof.

FIG. 6 shows a diagrammatic representation of one embodiment of a computing device in the exemplary form of a computer system 600 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 600 includes a processor 604 and a memory 608 that communicate with each other, and with other components, via a bus 612. Bus 612 may include any of several types of bus structures including, but not limited to, a memory bus, a memory controller, a peripheral bus, a local bus, and any combinations thereof, using any of a variety of bus architectures.

Processor 604 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 604 may be organized according to Von Neumann and/or Harvard architecture as a non-limiting example. Processor 604 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), and/or system on a chip (SoC)

Memory 608 may include various components (e.g., machine-readable media) including, but not limited to, a random-access memory component, a read only component, and any combinations thereof. In one example, a basic input/output system 616 (BIOS), including basic routines that help to transfer information between elements within computer system 600, such as during start-up, may be stored in memory 608. Memory 608 may also include (e.g., stored on one or more machine-readable media) instructions (e.g., software) 620 embodying any one or more of the aspects and/or methodologies of the present disclosure. In another example, memory 608 may further include any number of program modules including, but not limited to, an operating system, one or more application programs, other program modules, program data, and any combinations thereof.

Computer system 600 may also include a storage device 624. Examples of a storage device (e.g., storage device 624) include, but are not limited to, a hard disk drive, a magnetic disk drive, an optical disc drive in combination with an optical medium, a solid-state memory device, and any combinations thereof. Storage device 624 may be connected to bus 612 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 624 (or one or more components thereof) may be removably interfaced with computer system 600 (e.g., via an external port connector (not shown)). Particularly, storage device 624 and an associated machine-readable medium 628 may provide nonvolatile and/or volatile storage of machine-readable instructions, data structures, program modules, and/or other data for computer system 600. In one example, software 620 may reside, completely or partially, within machine-readable medium 628. In another example, software 620 may reside, completely or partially, within processor 604.

Computer system 600 may also include an input device 632. In one example, a user of computer system 600 may enter commands and/or other information into computer system 600 via input device 632. Examples of an input device 632 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 632 may be interfaced to bus 612 via any of a variety of interfaces (not shown) including, but not limited to, a serial interface, a parallel interface, a game port, a USB interface, a FIREWIRE interface, a direct interface to bus 612, and any combinations thereof. Input device 632 may include a touch screen interface that may be a part of or separate from display 636, discussed further below. Input device 632 may be utilized as a user selection device for selecting one or more graphical representations in a graphical interface as described above.

A user may also input commands and/or other information to computer system 600 via storage device 624 (e.g., a removable disk drive, a flash drive, etc.) and/or network interface device 640. A network interface device, such as network interface device 640, may be utilized for connecting computer system 600 to one or more of a variety of networks, such as network 644, and one or more remote devices 648 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 644, may employ a wired and/or a wireless mode of communication. In general, any network topology may be used. Information (e.g., data, software 620, etc.) may be communicated to and/or from computer system 600 via network interface device 640.

Computer system 600 may further include a video display adapter 652 for communicating a displayable image to a display device, such as display device 636. Examples of a display device include, but are not limited to, a liquid crystal display (LCD), a cathode ray tube (CRT), a plasma display, a light emitting diode (LED) display, and any combinations thereof. Display adapter 652 and display device 636 may be utilized in combination with processor 604 to provide graphical representations of aspects of the present disclosure. In addition to a display device, computer system 600 may include one or more other peripheral output devices including, but not limited to, an audio speaker, a printer, and any combinations thereof. Such peripheral output devices may be connected to bus 612 via a peripheral interface 656. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve systems and methods according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions, and additions may be made to that which is specifically disclosed herein without departing from the spirit and scope of the present invention.

What is claimed is:

1. A system for presenting an aliment from a modified nourishment scheme, the system comprising a computing device, the computing device configured to:
   receive a user attribute, wherein the user attribute comprises a user affliction;
   identify a nutrition requirement as a function of the user attribute wherein identifying further comprises:
      receiving a nutrition training set, wherein the nutrition training set correlates at least an aliment and at least a user attribute; and
      generating a nutrition requirement as a function of the user attribute, the nutrition training set, and a nutrition machine-learning process;
   receive a monitoring element;
   modify the nutrition requirement as a function of the monitoring element, wherein modifying further comprises;
      receiving a modification training set, wherein the modification training set includes a plurality of entries, and each entry of the plurality of entries correlates at least a monitoring element and at least nutrition outcome; and
      generating a modified nutrition requirement as a function of the monitoring element, the modification training set, and a modification machine-learning process;
   identify an aliment that fulfills the modified user nutrition requirement, wherein identifying an aliment that fulfills the modified user nutrition requirement comprises:
      hierarchically sorting aliments, wherein hierarchically sorting aliments comprises:
         determining a nourishment value corresponding to the modified nutrition requirement;
         creating a distance metric from the nourishment value to each candidate aliment of a plurality of candidate aliments;
         selecting at least one candidate aliment from the plurality of candidate aliments that minimizes the distance metric; and
         sorting each of the plurality of candidate aliments based on minimizing the distance metric; and
   present the aliment on a display device.

2. The system of claim 1, wherein the user attribute further comprises a user aliment history; and wherein identifying the nutrition requirement further comprises identifying the nutrition requirement as a function of the user aliment history.

3. The system of claim 2, wherein receiving the user aliment history further comprises receiving user aliment history from a food service datastore.

4. The system of claim 2, wherein receiving the user aliment history further comprises receiving user aliment history from a questionnaire.

5. The system of claim 2, wherein receiving the user aliment history further comprises receiving user aliment history from a databank as a function of a user engagement vector.

6. The system of claim 1, wherein receiving the user attribute further comprises receiving a user vigor status, and wherein identifying the nutrition requirement further comprises identifying the nutrition requirement as a function of the user vigor status.

7. The system of claim 1, wherein identifying the nutrition requirement further comprises receiving a user affliction as an input and outputting an aliment wherein the aliment relates to the user affliction.

8. The system of claim 1, wherein creating the distance further comprises creating a classifier distance.

9. A method for presenting an aliment from a modified nourishment scheme, the method further comprising:
   receiving, by a computing device, a user attribute, wherein the user attribute comprises a user affliction;
   identifying, by the computing device, a nutrition requirement as a function of the user attribute, wherein identifying further comprises:
      receiving a nutrition training set, wherein the nutrition training set correlates at least an aliment and at least a user attribute; and
      generating a nutrition requirement as a function of the user attribute, the nutrition training set, and a nutrition machine-learning process;
   receiving, by the computing device, a monitoring element;
   modifying, by the computing device, the nutrition requirement as a function of the monitoring element, wherein modifying further comprises;
      receiving a modification training set, wherein the modification training set includes a plurality of entries, and each entry of the plurality of entries correlates at least a monitoring element and at least nutrition outcome; and
      generating a modified nutrition requirement as a function of the monitoring element, the modification training set, and a modification machine-learning process;
   identifying, by the computing device, an aliment that fulfills the modified user nutrition requirement, wherein identifying the aliment that fulfills the modified user nutrition requirement comprises:
      hierarchically sorting, by the computing device, aliments, wherein hierarchically sorting aliments comprises:
         determining, by the computing device, a nourishment value corresponding to the modified nutrition requirement;
         creating, by the computing device, a distance metric from the nourishment value to each candidate aliment of a plurality of candidate aliments;
         selecting, by the computing device, at least one candidate aliment from the plurality of candidate aliments that minimizes the distance metric; and
         sorting, by the computing device, each of the plurality of candidate aliments based on minimizing the distance metric; and
   presenting, by the computing device, the aliment on a display device.

10. The method of claim 9, wherein the user attribute further comprises a user aliment history; and wherein identifying the nutrition requirement further comprises identifying the nutrition requirement as a function of the user aliment history.

11. The method of claim 10, wherein receiving the user aliment history further comprises receiving user aliment history from a food service datastore.

12. The method of claim 10, wherein receiving the user aliment history further comprises receiving user aliment history from a questionnaire.

13. The method of claim 10, wherein receiving the user aliment history further comprises receiving user aliment history from a databank as a function of a user engagement vector.

14. The method of claim 9, wherein the user attribute further comprises a user vigor status and wherein identifying the nutrition requirement further comprises identifying the nutrition requirement as a function of the user vigor status.

15. The method of claim 9, wherein identifying the nutrition requirement further comprises receiving a user affliction as an input and outputting an aliment that at least relates to the user affliction.

16. The method of claim 9, wherein creating the distance further comprises creating a classifier distance.

* * * * *